United States Patent
Gildersleeve et al.

(10) Patent No.: US 12,090,077 B2
(45) Date of Patent: *Sep. 17, 2024

(54) ANKLE BRACE

(71) Applicant: DJO, LLC, Carlsbad, CA (US)

(72) Inventors: Richard E. Gildersleeve, Carlsbad, CA (US); Robert J. Anderson, Charlotte, NC (US); Gregory Charles Berlet, Westerville, OH (US); W. Hodges Davis, Charlotte, NC (US); Tomas Buchhorn, Salching (DE)

(73) Assignee: DJO, LLC, Carlsbad, CA (US)

( * ) Notice: Subject to any disclaimer, the term of this patent is extended or adjusted under 35 U.S.C. 154(b) by 5 days.

This patent is subject to a terminal disclaimer.

(21) Appl. No.: 18/053,918

(22) Filed: Nov. 9, 2022

(65) Prior Publication Data

US 2023/0139433 A1 May 4, 2023

Related U.S. Application Data

(63) Continuation of application No. 16/330,977, filed as application No. PCT/US2017/050820 on Sep. 8, 2017, now Pat. No. 11,517,462.

(Continued)

(51) Int. Cl.
*A61F 5/01* (2006.01)
*A43B 7/14* (2022.01)
(Continued)

(52) U.S. Cl.
CPC .............. *A61F 5/0111* (2013.01); *A43B 7/14* (2013.01); *A43B 23/22* (2013.01); *A61F 5/0585* (2013.01);
(Continued)

(58) Field of Classification Search
CPC .. A61F 5/01; A61F 5/0111; A61F 5/05; A61F 5/0585; A61F 2005/0165; A61F 2005/0172; A61F 5/058; A43B 7/20
See application file for complete search history.

(56) References Cited

U.S. PATENT DOCUMENTS

| | | |
|---|---|---|
| 4,878,504 A | 11/1989 | Nelson |
| 5,050,620 A | 9/1991 | Cooper |

(Continued)

OTHER PUBLICATIONS

International Search Report and Written Opinion dated Nov. 7, 2017, in PCT/US17/50820.

(Continued)

*Primary Examiner* — Keri J Nelson
(74) *Attorney, Agent, or Firm* — KNOBBE, MARTENS, OLSON & BEAR LLP

(57) ABSTRACT

An ankle brace for treating or preventing a high ankle sprain is disclosed. The ankle brace includes a body configured to be worn over an ankle. A tightening mechanism is attached to the body and configured to tighten the body around a wearer's lower leg to prevent distal ends of the tibia and fibula from separating. A torsion strap is attached to the body and configured to wrap from a fifth metatarsal to a medial malleolus to limit external rotation of the foot. The ankle brace can include lateral and medial straps for limiting eversion and inversion of the foot. The ankle brace can include heat moldable lateral and medial support plates.

20 Claims, 10 Drawing Sheets

Related U.S. Application Data

(60) Provisional application No. 62/385,824, filed on Sep. 9, 2016.

(51) Int. Cl.
    *A43B 23/22*     (2006.01)
    *A61F 5/058*     (2006.01)
    *A43B 7/20*     (2006.01)
    *A43C 11/14*     (2006.01)

(52) U.S. Cl.
CPC .............. *A43B 7/20* (2013.01); *A43C 11/1493* (2013.01); *A61F 2005/0165* (2013.01); *A61F 2005/0172* (2013.01); *A61F 2005/0174* (2013.01); *A61F 2005/0179* (2013.01)

(56) References Cited

U.S. PATENT DOCUMENTS

| | | | |
|---|---|---|---|
| 5,370,133 A | 12/1994 | Darby et al. | |
| 5,501,659 A | 3/1996 | Morris | |
| 5,621,985 A | 4/1997 | Frost | |
| 5,720,715 A | 2/1998 | Eriksson | |
| 5,795,316 A | 8/1998 | Gaylord | |
| 5,853,381 A * | 12/1998 | Stevenson | A61F 5/0111 602/65 |
| 5,902,259 A | 5/1999 | Wilkerson | |
| 6,270,468 B1 | 8/2001 | Townsend et al. | |
| 6,602,215 B1 | 8/2003 | Richie, Jr. | |
| 8,591,440 B2 | 11/2013 | Logue et al. | |
| 8,821,427 B1 * | 9/2014 | Weber | A61F 5/0111 602/23 |
| 11,517,462 B2 | 12/2022 | Gildersleeve et al. | |
| 2005/0274045 A1 | 12/2005 | Selner | |
| 2007/0049857 A1 | 3/2007 | Qunn et al. | |
| 2008/0306422 A1 | 12/2008 | McChesney et al. | |
| 2009/0076428 A1 | 3/2009 | Kay | |
| 2012/0004587 A1 | 1/2012 | Nickel et al. | |
| 2012/0078152 A1 | 3/2012 | Robertson | |
| 2014/0188026 A1 | 7/2014 | Gaylord et al. | |
| 2015/0216704 A1 | 8/2015 | Madden et al. | |

OTHER PUBLICATIONS

Extended European Search Report dated Mar. 9, 2020, in application No. 17849676.6.

* cited by examiner

ANKLE BRACE

INCORPORATION BY REFERENCE TO ANY PRIORITY APPLICATIONS

This application is a continuation of U.S. application Ser. No. 16/330,977, filed Mar. 6, 2019, which claims priority to PCT Application No. PCT/US2017/050820, filed Sep. 8, 2017, which claims the benefit of U.S. Provisional Application No. 62/385,824, filed Sep. 9, 2017, and each of the above-referenced disclosures are incorporated herein, by reference, in their entirety. Any and all applications for which a foreign or domestic priority claim is identified in the Application Data Sheet as filed with the present application are hereby incorporated by reference under 37 CFR 1.57.

BACKGROUND

Field

This disclosure relates to ankle braces. In particular, this disclosure relates to ankle braces for high ankle sprains.

Description

An ankle sprain is a common injury. There are several types of ankle sprains, including inversion (lateral) ankle sprains, eversion (medial) ankle sprains, and high (syndesmotic) ankle sprains. Although occurring with less frequency than other types of ankle sprains, high ankle sprains can be particularly painful.

A high ankle sprain is a sprain of the ligaments that connect the tibia and fibula in the lower leg, above the ankle. High ankle sprains commonly occur from outward, external rotation or twisting of the foot. In some instances, the outward, external rotation or twisting of the foot that causes a high ankle sprain can be coupled with concurrent eversion, dorsiflexion, or plantarflexion of the foot.

SUMMARY

Ankle braces and methods of use therefore are disclosed herein. The ankle braces can be configured and used to treat and/or prevent high ankle sprains. In some embodiments, the ankle braces include a tightening mechanism configured to limit spreading of the distal ends of the tibia and fibula. In some embodiments, the ankle braces include a torsion strap configured to limit external rotation of the foot. In some embodiments, the ankle braces include lateral and medial straps and/or lateral and medial support plates to further control movement of the ankle. For example, the lateral and medial straps and/or lateral and medial support plates can be configured and positioned to limit or prevent internal and/or external rotation of the foot, eversion and/or inversion of the foot, and/or plantarflexion and/or dorsiflexion of the foot.

In a first aspect, an ankle brace for a high ankle sprain is disclosed. The ankle brace includes a body configured in size and shape to be worn on an ankle, the body including a foot portion and a lower leg portion; a first tightening mechanism attached to the lower leg portion of the body, the first tightening mechanism actuable to tighten the lower leg portion of the body; and a torsion strap having a distal end connected to a lateral side of the foot portion of the body, the torsion strap configured to wrap around the body from the distal end over or adjacent to a medial malleolus.

In some embodiments, the torsion strap is configured to limit external rotation of a foot when the brace is worn. In some embodiments, the torsion strap connects the fifth metatarsal and the medial malleolus when the brace is worn. In some embodiments, the torsion strap comprises an elastomeric material. In some embodiments, the first tightening mechanism comprises: a reel attached to a first portion of the lower leg portion; a lace guide attached to a second portion of the lower leg portion; and a lace extending between the reel and the lace guide; wherein the reel is actuable to tighten the lace to bring the first portion toward the second portion. In some embodiments, the first tightening mechanism is attached to the lower leg portion at a position above the medial malleolus. In some embodiments, the ankle brace further includes a second tightening mechanism attached to the lower leg portion at a position below the first tightening mechanism. In some embodiments, the second tightening mechanism comprises a strap configured to wrap around the lower leg portion. In some embodiments, the second tightening mechanism is positioned on the lower leg portion so as to overlap the medial malleolus.

In some embodiments, the ankle brace further includes a medial support plate attached to the body, the medial support plate extending over the medial malleolus. In some embodiments, the medial support plate comprises a heat formable material. In some embodiments, the ankle brace further includes a lateral support plate attached to the body, the lateral support plate extending over a lateral malleolus. In some embodiments, the lateral support plate comprises a heat formable material.

In some embodiments, the ankle brace further includes a medial strap having a distal end connected to the foot portion on the medial side of the body and a proximal end removably attachable to the medial side of the lower leg portion. In some embodiments, the medial strap is tightenable to limit eversion of the foot. In some embodiments, the ankle brace further includes a lateral strap having a distal end connected to the foot portion on the lateral side of the body and a proximal end removably attachable to the lateral side of the lower leg portion. In some embodiments, the lateral strap is tightenable to limit inversion of the foot.

In some embodiments, the ankle brace further includes a medial buttress removably attachable to the foot portion of the body above the medial malleolus, the medial buttress comprising an arcuate pad configured to partially surround the medial malleolus. In some embodiments, the ankle brace further includes a lateral buttress removably attachable to the foot portion of the body above the lateral malleolus, the lateral buttress comprising an arcuate pad configured to partially surround the lateral malleolus. In some embodiments, the ankle brace further includes a rigid footplate attached to the body, the rigid footplate configured to partially surround a calcaneus of the foot when worn.

In another aspect, a method for treating a high ankle sprain with an ankle brace is disclosed. The method includes positioning the ankle brace over an ankle; tightening a first tightening mechanism of the ankle brace around a lower leg above the ankle to prevent the distal ends of the tibia and fibula from separating; and connecting a fifth metatarsal region of a foot to a medial malleolus of the foot with a torsion strap to limit external rotation of the foot.

In some embodiments, the first tightening mechanism is positioned on the ankle brace above the medial malleolus. In some embodiments, the method further includes tightening a second tightening mechanism of the ankle brace around the lower leg, wherein the second tightening mechanism is positioned on the ankle brace below the first tightening mechanism.

In some embodiments, the method further includes tightening a medial strap of the ankle brace to limit eversion of the foot. In some embodiments, the method further includes tightening a lateral strap of the ankle brace to limit inversion of the foot. In some embodiments, the method further includes attaching a medial support plate to the ankle brace, the medial support plate extending over the medial malleolus. In some embodiments, the method further includes heat molding the medial support plate to conform to anatomy of the ankle. In some embodiments, the method further includes attaching a lateral support plate to the ankle brace, the lateral support plate extending over a lateral malleolus. In some embodiments, the method further includes heat molding the lateral support plate to conform to anatomy of the ankle. In some embodiments, the ankle brace comprises the ankle brace of the first aspect.

BRIEF DESCRIPTION OF THE DRAWINGS

The features and advantages of the ankle braces described herein will become more fully apparent from the following description and appended claims, taken in conjunction with the accompanying drawings. These drawings depict only several embodiments in accordance with the disclosure and are not to be considered limiting of its scope. In the drawings, similar reference numbers or symbols typically identify similar components, unless context dictates otherwise. The drawings may not be drawn to scale.

DETAILED DESCRIPTION

Figure 1:
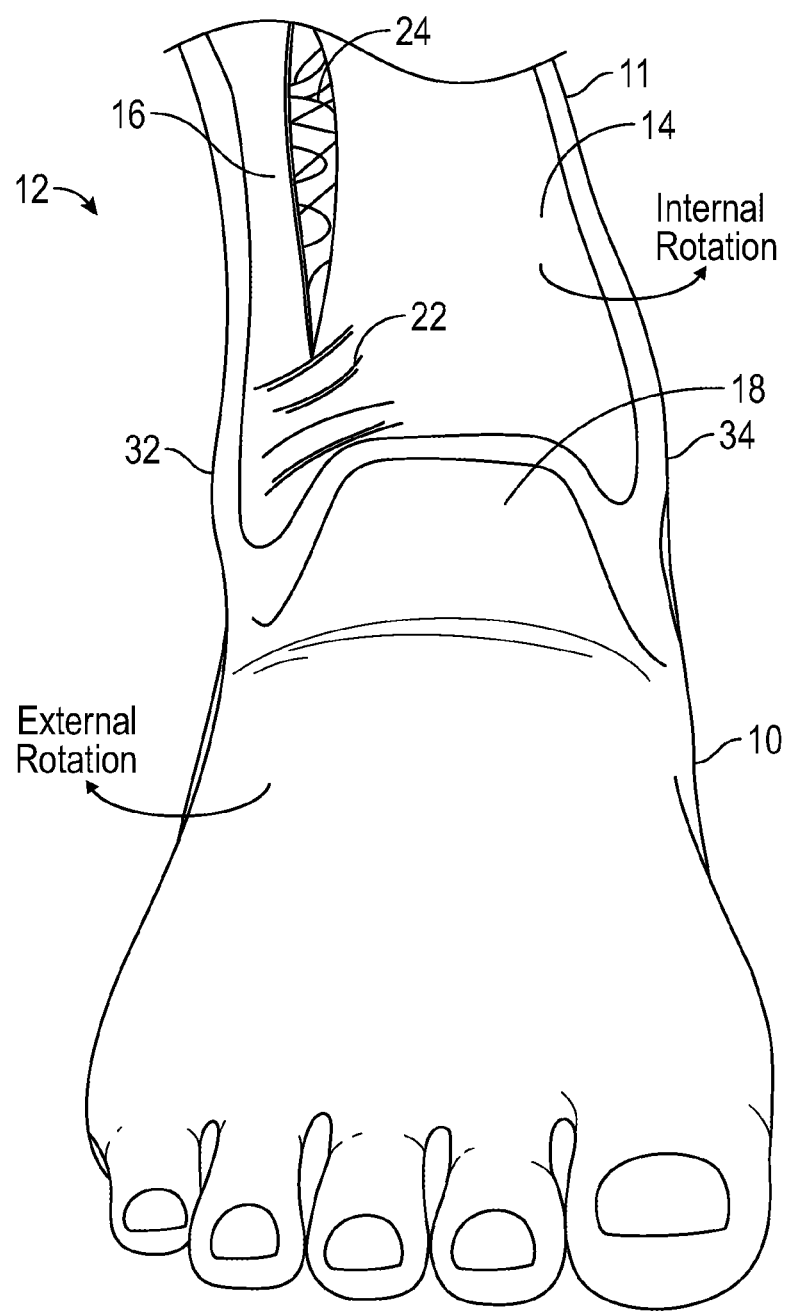
FIG. 1 is an anterior view of a foot and lower leg, illustrating a partial view of the anatomy of an ankle.

FIG. 1 is an anterior view of a foot 10 and lower leg 11, illustrating a partial view of the anatomy of an ankle 12. The ankle 12 permits a wide range of motion between the foot 10 and the lower leg 11. For example, the ankle 12 permits internal and external rotation of the foot 10 relative to the lower leg 11, eversion and inversion of the foot 10 relative to the lower leg 11, and plantarflexion and dorsiflexion of the foot 10 relative to the lower leg 11. The ankle 12 includes a joint formed between the distal ends of the tibia 14 and fibula 16 and the proximal end of the talus 18. Distal ends of the tibia 14 and fibula 16 articulate on the proximal end of the talus 18 during motion of the ankle 12.

Lower ligaments 22 connect the distal ends of the tibia 14 and fibula 16. Lower ligaments 22 include, for example, the anterior inferior tibiofibular ligament and the posterior inferior tibiofibular ligament. The lower ligaments 22 resist separation of the distal ends of the tibia 14 and fibula 16. Upper ligaments 24 also extend between and connect the tibia 14 and fibula 16. The upper ligaments 24 include, for example, the syndesmotic ligaments which span the syndesmosis between the lateral aspect of the tibia 14 and the medial aspect of the fibula 16 between ankle 12 and the knee. Like the lower ligaments 22, the upper ligaments 24 resist separation of the tibia 14 and fibula 16.

High ankle sprains are sprains of the lower ligaments 22 and/or upper ligaments 24. Low-high ankle sprains, a subset of high ankle sprains, are sprains of only the lower ligaments 22. The lower ligaments 22 and/or upper ligaments 24 can be sprained by separation of the distal ends of the tibia 14 and fibula 16, which stretches and/or tears the lower ligaments 22 and/or upper ligaments 24.

High ankle sprains are commonly caused by external rotation of the foot 10 relative to the lower leg 11 and/or internal rotation of the lower leg 11 relative to foot 10. In some instances of high ankle sprains, the external rotation of the foot 10 and/or internal rotation of the lower leg 11 that causes the sprain is coupled with and compounded by eversion, dorsiflexion, or plantarflexion of the foot 10. For example, it has been observed that greater than 50% of all high ankle sprain injuries involve eversion of the foot 10, approximately 50% of all high ankle sprain injuries involve dorsiflexion of the foot 10, and approximately 10% of all high ankle sprain injuries involve plantarflexion of the foot 10 (in addition to the external rotation of the foot 10 and/or internal rotation of the lower leg 11).

In some instances of high ankle sprains, the motions described above alter the relative positions of the distal ends of the tibia 14 and fibula 16 and the proximal end of the talus 18. For example, as the foot 10 rotates externally, the distal ends of the tibia 14 and fibula 16 are presented with an increasingly wider aspect of the proximal end of the talus 18. This can cause separation of the distal ends of the tibia 14 and fibula 16 resulting in a sprain of the lower ligaments 22 and/or upper ligaments 24. Other causes of high ankle sprains are also possible.

The ankle braces described herein are configured to treat and/or prevent high ankle sprains. In some instances, the ankle braces can be worn post-injury to, for example, aid in rehabilitation of the injury, reduce pain and discomfort associated with the injury, and/or reduce the likelihood of further injury. In some instances, the ankle braces can be worn pre-injury in an effort to reduce the likelihood of experiencing a high ankle sprain.

As such, the ankle braces described herein can be configured to prevent, limit, or reduce one or more of the causes of high ankle sprains described above. For example, the ankle braces can be configured to prevent, limit, or reduce separation of the distal ends of the tibia 14 and fibula 16. Alternatively or additionally, the ankle braces can be configured to prevent, limit, or reduce one or more of the motions described above that commonly cause high ankle sprains. For example, the ankle braces can be configured to prevent, limit, or reduce external rotation of the foot 10 relative to the lower leg 11 and/or internal rotation of the lower leg 11 relative to foot 10. In some instances, the ankle braces can be configured to additionally or alternatively prevent, limit, or reduce eversion, dorsiflexion, and/or plantarflexion of the foot 10.

These and other features of the ankle braces described herein will be further described with reference to the remaining figures, which illustrate several embodiments of ankle braces. These embodiments are not intended to be limiting, and various modifications, variations, combinations, etc., of the features of these embodiments are possible and within the scope of this disclosure.

Figure 2A:
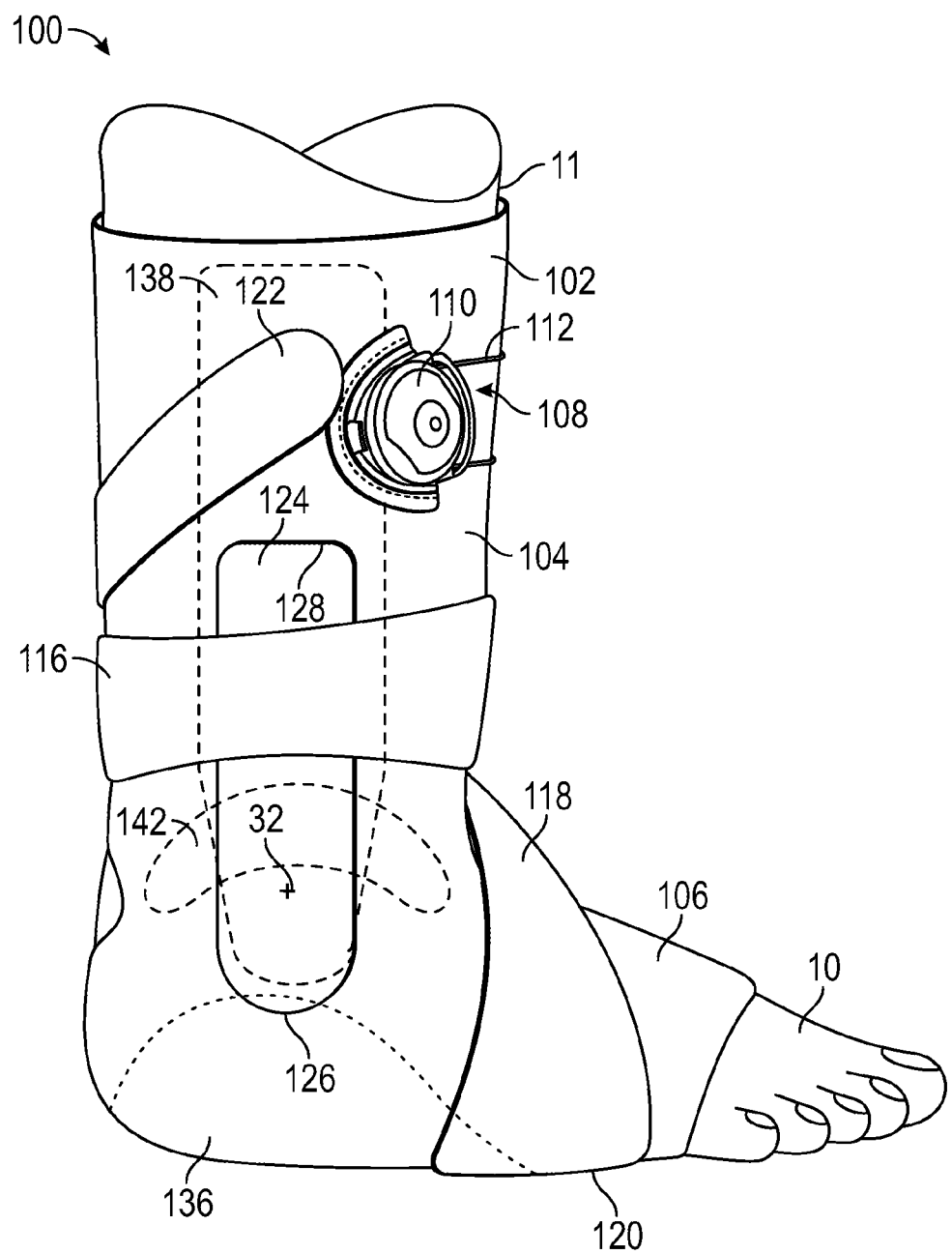
FIG. 2A is a lateral view of an embodiment of an ankle brace worn on an ankle.
Figure 2B:
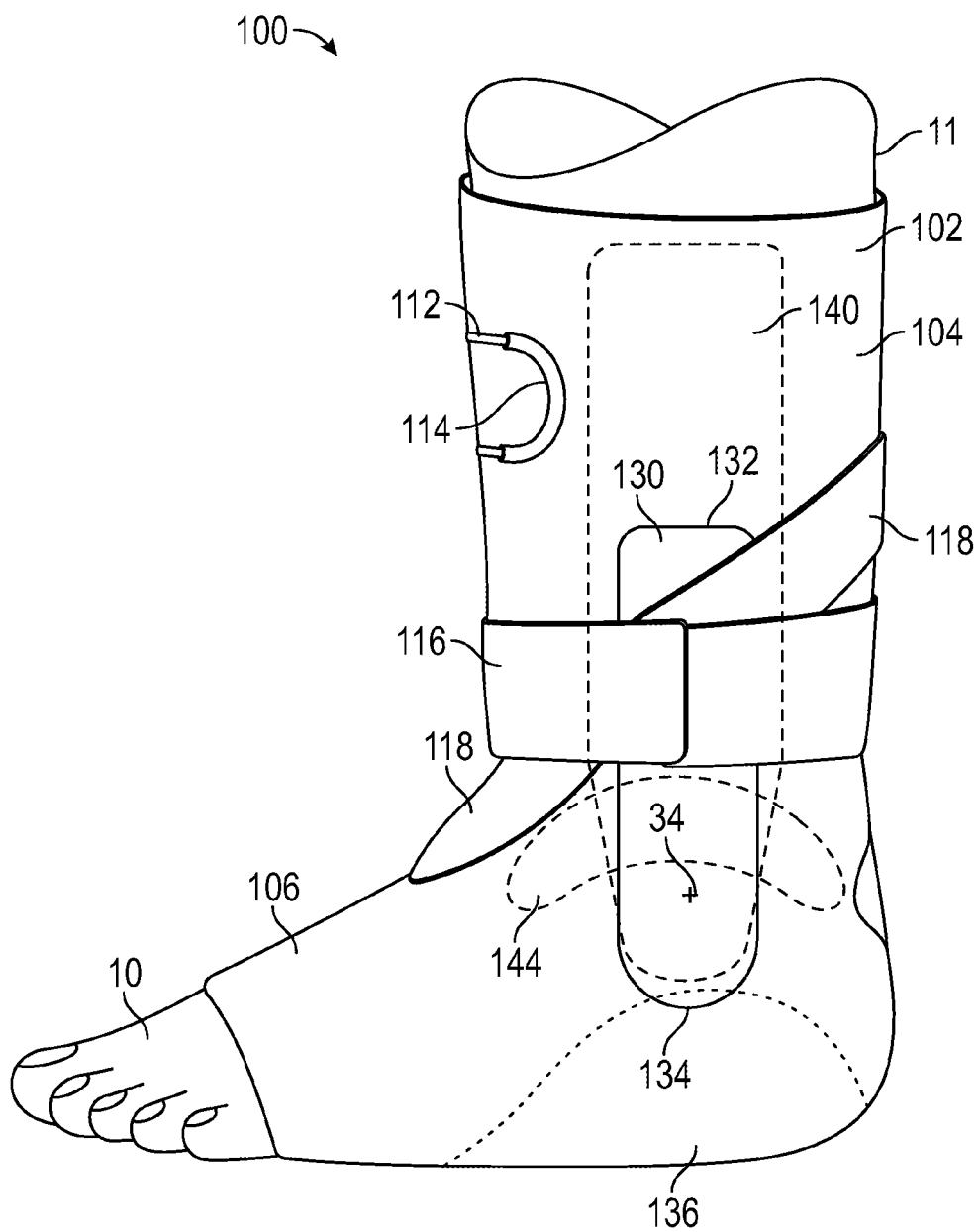
FIG. 2B is a medial view of the ankle brace of FIG. 2A.

FIGS. 2A and 2B are lateral and medial views, respectively, of an embodiment of an ankle brace 100. As will be described in detail below, the brace 100 is configured for treatment and/or prevention of high ankle sprains. Although this disclosure primarily refers to high ankle sprains, the brace 100 may also be useful in treating and/or preventing other types of ankle sprains (such as inversion ankle sprains and/or eversion ankle sprains) and/or other types of ankle, foot, and/or lower leg injuries. FIGS. 2A and 2B illustrate an example of the brace 100 configured to be worn on a right ankle. A mirror image of the illustrated brace 100 can be worn on a left ankle.

As shown in FIGS. 2A and 2B, the brace 100 is configured to be worn on an ankle. The brace 100 includes a body 102, which may include or more layers of material. The body 102 can be a sock, wrap, cover, housing, etc., configured to be worn on the ankle. The body 102 can be made from a flexible material, such as fabric. In some examples, the fabric comprises a four-way stretch fabric. The flexible material can comprise, for example, one or more of a knit nylon spandex blend, knit polyester spandex blend, fabrics of nylon, polyester, lycra, or rubberized materials. The body 102 can include an inside surface and an outside surface.

In use, the inside surface may contact the body of the wearer. In some examples, the inside surface is lined with padding or foam. The padding or foam may increase the comfort of the brace 100. In some examples, the inside surface is lined with an open cell foam, such as a urethane open cell foam. The inside surface of the body 102 can also include one or more portions or regions of a hookable material (e.g., a hook material or a loop material of a hook and loop fastener). This may allow attachment of various accessories inside the brace 100. As will be described in greater detail below, such accessories may include a lateral support plate 138, a medial support plate 140, a lateral buttress 142, and/or a medial buttress 144, among other accessories. The accessories may comprise a material configured to removably attach to the hookable material. The accessories can thus be placed in any desired position or orientation on the hookable material. In some examples, the entire inner surface of the body 102 comprises a hookable material.

In some examples, the outside surface of the body 102 comprises a hookable material (e.g., a hook material or a loop material of a hook and loop fastener). The hookable material may cover the entirety of the outside surface. The hookable material may cover only certain portions or regions of the outside surface. The hookable material may be configured to allow attachment of various straps or other attachment or fastening mechanisms, such as a first tightening mechanism 108, a second tightening mechanism 116, a torsion strap 118, a lateral strap 124, and/or a medial strap 130, as will be described below in greater detail below.

In the illustrated embodiment, the body 102 includes a leg portion 104 and a foot portion 106. The leg portion 104 is configured to receive a portion of a wearer's lower leg 11. The leg portion 104 extends from the ankle up the lower leg 11 towards the wearer's knee. The leg portion 104 can extend 25%, 35%, 40%, 50%, 55%, 65%, or 75% the distance between the ankle and the knee, although other lengths are also possible. The leg portion 104 may completely surround (e.g., wrap around) the wearer's leg. For example, the leg portion may comprise a looped (e.g., a generally cylindrical) section into which the lower leg 11 is inserted, such as a sock. As another example, the leg portion 104 can comprise an open (e.g., U-shaped) section that can be wrapped around the wearer's leg and then closed via flaps, ties, laces, straps, hook and loop material or other suitable fastening mechanisms. In some examples, the wearer inserts the lower leg 11 through the open section (e.g., the open end of the U-shape) to put on the brace 100. The open section can be positioned on an anterior, posterior, medial, or lateral side of the body 102. FIGS. 3A-4D illustrate an embodiment that includes an open section that is positioned on a posterior side. In another example, the leg portion 104 extends only partially around the wearer's leg.

The foot portion 106 is configured to receive a portion of the wearer's foot 10. In the illustrated embodiment, the foot portion 106 extends approximately to the midfoot. The foot portion 106 may include an opening to allow a distal end of the foot to extend therethrough. The foot portion 106, in some examples, does not cover the toes. The foot portion 106 may completely surround (e.g., wrap around) the wearer's foot 10. For example, the foot portion 106 may comprise a looped (e.g., a generally cylindrical, such as a sock or sleeve) section though which the foot 10 extends. An embodiment of a brace that includes such a looped foot section is shown in FIGS. 2A-3B. As another example, the foot portion 106 can comprise an open (e.g., U-shaped) section that can be wrapped around the wearer's foot 10 and then closed via flaps, ties, laces, straps, hook and loop material or other suitable fastening mechanisms. In some examples, the wearer inserts the foot 10 through the open section (e.g., the open end of the U-shape) to put on the brace 100. The open section can be positioned on an anterior, posterior, medial, or lateral side of the body 102.

The brace 100 can also include a first tightening mechanism 108. The first tightening mechanism 108 can be positioned on the leg portion 104 of the body 102. The first tightening mechanism 108 is configured to tighten the leg portion 104 around the lower leg 11 of the wearer. For example, in some embodiments, the first tightening mechanism 108 can be positioned as follows. The first tightening mechanism 108 can be positioned approximately 0.5 to 6 inches, 1 to 5 inches, 2 to 4 inches, or about 3 inches above the distal ends of the tibia 14 and fibula 16 when the brace 100 is worn. The first tightening mechanism 108 can be positioned approximately 1, 2, 3, 4, 5, 6, or more inches above the distal ends of the tibia 14 and fibula 16 when the brace 100 is worn. The first tightening mechanism 108 can be positioned approximately 0.5 to 6 inches, 1 to 5 inches, 2 to 4 inches, or about 3 inches above the lateral malleolus 32 and/or medial malleolus 34 when the brace 100 is worn. The first tightening mechanism 108 can be positioned approximately 1, 2, 3, 4, 5, 6, or more inches above the lateral malleolus 32 and/or medial malleolus 34 when the brace 100 is worn. As mentioned above, the first tightening mechanism 108 is configured to tighten the leg portion 104 around the lower leg 11 of the wearer. Thus, the first tightening mechanism 108 can provide a compressive force that holds the distal ends of the tibia 14 and fibula 16 and/or prevents spreading of the tibia 14 and fibula 16.

In the illustrated embodiment, the first tightening mechanism 108 comprises a reel 110, a lace 112, and lace guide 114. The reel 110 can be positioned on a first side (e.g., one of the lateral or medial sides) of the body 102 (e.g., FIG. 2A) and the lace guide 114 can be positioned on a second, opposite side (e.g., the other of the lateral or medial side as illustrated in FIG. 2B). The lace 112 extends between the reel 110 and the lace guide 114. Although a particular lace pattern is illustrated in the figures, this disclosure should not be limited to only the illustrated embodiments. A wide variety of lace patterns, including a plurality of reels, laces, and lace guides are possible and within the scope of this disclosure. The reel 110 can be configured to tighten the lace 112 when the reel 110 is actuated. Thus, as the reel 110 is actuated, the reel 110 and the lace guide 114 are brought closer together by the tightening lace 112, resulting in a tightening of the leg portion 104 around the lower leg 111. In some embodiments, the first tightening mechanism 108, including the reel 110, lace 112, and lace guide 114, comprises a cable reel attachment system, such as the Boa System distributed by Boa Technology Inc.

Alternatively to the reel 110, lace 112, and lace guide 114 illustrated in the figures, the first tightening mechanism 108 can comprise any other type of tightening mechanisms, such as straps (e.g., fabric or rubber straps of elastic or inelastic material, including hook and loop fasteners), ratchet mechanisms, traditional lace systems (e.g., similar to shoe laces), etc.

In the illustrated embodiment, the brace 100 also includes a second tightening mechanism 116. The second tightening mechanism 116 is positioned on the leg portion 104 of the body 102. The second tightening mechanism 116 can be positioned below the first tightening mechanism 108 and the distal ends of the tibia 14 and fibula 16. The second tightening mechanism 116 can be positioned below the first tightening mechanism 108 and lateral malleolus 32 and/or medial malleolus 34. The second tightening mechanism 116 can be positioned to overlap or cover the distal ends of the tibia 14 and fibula 16 when the brace 100 is worn. The second tightening mechanism 116 can be positioned to overlap or cover the lateral malleolus 32 and/or medial malleolus 34 when the brace 100 is worn.

Similar to the first tightening mechanism 108, the second tightening mechanism 116 is configured to tighten the leg portion 104 around the lower leg 11 of the wearer. Thus, the second tightening mechanism 116 can also provide a compressive force that holds the distal ends of the tibia 14 and fibula 16 and/or prevents spreading of the tibia 14 and fibula 16.

In the illustrated embodiment, the second tightening mechanism 116 comprises a strap, which wraps around the leg portion 106. The strap can comprise a strip of fabric, rubber, other flexible material. The strap can comprise an elastic or inelastic material. The strap can include portions of hook and loop material such that the strap can be attached to itself and/or to the outer surface of the body 102 to secure the strap. For example, an inside surface of the strap (e.g., disposed towards the body 102) can include a hook material and the outside surface of the strap can include a loop material. The inside surface can thus attach to the outside surface of the body 102 and/or to the outside surface of the strap as the strap is wrapped around the brace 100.

Although the second tightening mechanism 116 is illustrated as a strap in the figures, the second tightening mechanism 116 can comprise any other type of tightening mechanism, such as a ratchet mechanism, a traditional lace system (e.g., similar to shoe laces), a reel and cable system (e.g., a Boa System), etc. The second tightening mechanism 116 need not be included in all embodiments.

The brace 100 can also include a torsion strap 118, as illustrated. As shown in FIGS. 2A and 2B, the torsion strap 118 includes a distal end 120 and a proximal end 122. The torsion strap 118 is configured limit, restrict, or prevent external rotation of the foot 10. For example, in the illustrated example, the distal end 120 is fixedly attached to the foot portion 106 of the body 102. The distal end 120 can be fixedly attached to the foot portion 106 at a region proximal to the fifth metatarsal of the foot 10, when the brace 100 is worn. In some examples, the distal end 120 can be fixedly attached to the foot portion 106 at a region proximal to the fifth metatarsal of the foot 10 on the lateral side of the brace 100. In some examples, the distal end is attached to the foot portion 106 on a bottom or sole side of the brace 100. From the distal end 120, the torsion strap 118 can be configured to wrap around the brace 100 as shown in FIGS. 2A and 2B. For example, from the distal end 120, the torsion strap 118 can extend up the medial side of the foot 10, across the dorsal of the foot 10 to the medial side of the foot 10, and around the medial side of the ankle (passing over or higher than the lateral malleolus 34 (see FIG. 2B). In the illustrated embodiment, the torsion strap 118 continues around the posterior portion of the lower leg and is secured to the lateral side of the brace 100 by a fastener (e.g., a hook and loop fastener) at the proximal end 120. In some examples, the torsion strap 118 is configured to connect the fifth metatarsal to the medial malleolus 34. In some examples, connecting the fifth metatarsal to the medial malleolus 34 limits, reduces, or prevents external rotation of the foot 10.

The torsion strap 118 can comprise an elastomeric material. In one example, the torsion strap 118 comprises silicone. The torsion strap 118 may comprise a stretchable material. The stretchable material may limit external rotation of the foot 10 while still providing some motion of the foot. For example, the torsion strap 118 may limit external rotation of the foot 10 to 5, 10, 15, 20, 25, 30, 35, 40, or 45 degrees, as well as to other angles higher and lower than the listed values or to any range between any of the listed values. In an alternative embodiment, the torsion strap 118 can be made from an inelastic material, such as a non-stretchable fabric, plastic or rubber material. This may fully limit external rotation of the foot 10.

In some instances, a wearer may control the degree to which the torsion strap 118 limits or reduces external rotation of the foot 10 by adjusting how tightly the torsion strap 118 is wrapped around the brace 100. For example, wrapping the torsion strap 118 more tightly around the brace 100 may limit or reduce external rotation of the foot 10 to a greater degree than wrapping the torsion strap 118 less tightly around the brace 100. Alternatively or additionally, in some instances, a wearer may control the degree to which the torsion strap 118 limits or reduces external rotation of the foot 10 by adjusting the placement of the torsion strap 118 as it wraps around the brace 100. For example, wrapping the torsion strap 118 such that it passes above (e.g., higher) than the medial malleolus 34 may provide greater reduction or limitation of external rotation of the foot 10 than when the torsion strap 118 is wrapped directly over the medial malleolus 34.

In some examples, a wearer may wrap the torsion strap 118 under the second tightening mechanism 116 as illustrated in FIGS. 2A and 2B. In some examples, a wearer may wrap the torsion strap 118 over the second tightening mechanism 116. In some examples, the torsion strap 118 may extend over or under a portion of the first tightening mechanism 108.

The brace 100 may also include a lateral strap 124 (see FIG. 2A) and/or a medial strap 130 (see FIG. 2B). The lateral strap 124 and/or medial strap 130 can be positioned and configured to limit or prevent eversion and or inversion of the foot 10. For example, the lateral strap 124 extends between a distal end 126 and a proximal end 128. The distal end 126 can be fixedly attached to body 102 at a point on the lateral side of the brace 100 below the lateral malleolus 32. From the distal end 126, the lateral strap 124 extends proximally up the lateral side of the brace 100. The proximal end 128 of the lateral strap 124 can be removably attached (for example, via a hook and loop fastener) to the lateral side of the leg portion 104 of body 102. In the illustrated example, the lateral strap 124 can be tightened by attaching the proximal end 128 further up the brace 100. Tightening the lateral strap 124 can reduce or limit eversion of the foot 10.

Similarly, the medial strap 130 extends between a distal end 134 and a proximal end 132. The distal end 134 can be fixedly attached to body 102 at a point on the medial side of the brace 100 below the medial malleolus 34. From the distal end 134, the medial strap 130 extends proximally up the medial side of the brace 100. The proximal end 132 of the medial strap 130 can be removably attached (for example, via a hook and loop fastener) to the medial side of the leg portion 104 of body 102. In the illustrated example, the medial strap 130 can be tightened by attaching the proximal end 132 further up the brace 100. Tightening the medial strap 130 can reduce or limit inversion of the foot 10. Thus, by adjusting the lateral strap 124 and the medial strap 130, a wearer can control inversion and eversion of the foot 10.

The lateral strap 124 and/or the medial strap 130 can be made from an inelastic material, such as a non-stretchable fabric, plastic or rubber material. Alternatively, the lateral strap 124 and/or the medial strap 130 can comprise an elastomeric material. In one example, the lateral strap 124 and the medial strap 130 comprise silicone. The lateral strap 124 and the medial strap 130 may comprise a stretchable material. The lateral strap 124 and/or the medial strap 130 may limit inversion and/or eversion of the foot 10 to 5, 10, 15, 20, or 25 degrees, as well as to other angles higher and lower than the listed values or to any range between any of the listed values. In some examples, one or both of the lateral strap 124 and the medial strap 130 can be omitted.

In some instances, the lateral strap 124 and/or the medial strap 130 can be positioned below the second tightening mechanism 116 and the torsion strap 118 as illustrated. In some instances, the lateral strap 124 and/or the medial strap 130 can extend over one or both of the second tightening mechanism 116 and the torsion strap 118. Although the lateral strap 124 and the medial strap 130 are illustrated in FIGS. 2A and 2B extending only partway up the brace 100, in some instances, the lateral strap 124 and/or the medial strap 130 can extend all the way up the brace 100.

The brace 100 may include a footplate 136. The footplate 136 can be positioned on the inside of the body 102. In some examples, the footplate 136 is positioned between the outer surface and the inner surface of the body 102. Accordingly, in FIGS. 2A and 2B, the footplate 136 is illustrated using dashed lines. In some examples, the footplate 136 can be positioned on the outer surface of the body 102. The footplate 136 can be formed from a rigid material, such as plastic, metal, or similar materials. In some examples, the footplate 136 is formed from molded nylon. In some examples, the footplate 136 is made from a material that is less than 2 mm thick, less than 1 mm thick, less than 0.5 mm thick, or thinner. The footplate 136 can extend below a portion of the sole of the foot 10. For example, the footplate 136 can extend below the sole of the foot 10 between the heel and the midfoot. The footplate 136 may also extend partially up the medial and/or lateral sides of the foot 10 to partially surround the calcaneus. In some examples, the footplate 136 is permanently attached to the brace 100. In some embodiments, the footplate 136 is removably attached to brace 100. For example, the footplate 136 can be insertable into a pocket in the body 102 or attached to the inner or outer surfaces of the body 102 by fasteners (such as hook and loop fasteners).

The brace 100 can include a lateral support plate 138 (see FIG. 2A) and/a medial support plate 140 (see FIG. 2B). The lateral support plate 138 extends along the lateral side of the brace 100, for example, from a position below the lateral malleolus 32 to a position above the lateral malleolus 32. The lateral plate 138 may have various dimensions, for example, suitable to the size for the brace 100 and/or the ankle or leg of the wearer of the brace 100. The lateral support plate 138 may be at least 2, 3, 4, 5, 6, 8, 10, or 12 inches long, as well as other lengths higher or lower than the listed values or any range of lengths between any of the listed values. The lateral support plate 138 may be at least 0.5, 1, 1.5, 2 or 2.5 inches wide, as well as other widths higher or lower than the listed values or any range of widths between any of the listed values. The medial support plate 140 extends along the medial side of the brace 100, for example, from a position below the medial malleolus 34 to a position above the medial malleolus 34. The medial support plate 140 may be at least 2, 3, 4, 5, 6, 8, 10, or 12 inches long, as well as other lengths higher or lower than the listed values or any range of lengths between any of the listed values. The medial support plate 140 may be at least 0.5, 1, 1.5, 2 or 2.5 inches wide, as well as other widths higher or lower than the listed values or any range of widths between any of the listed values.

The lateral and/or medial support plates 138, 140 can be positioned on the inside of the body 102. In some examples, the lateral and/or medial support plates 138, 140 are positioned between the outer surface and the inner surface of the body 102. Accordingly, in FIGS. 2A and 2B, the lateral and/or medial support plates 138, 140 are illustrated using dashed lines. In some examples, the lateral and/or medial support plates 138, 140 can be positioned on the outer surface of the body 102. In some examples, the lateral and/or medial support plates 138, 140 are permanently attached to the brace 100. In some embodiments, the lateral and/or medial support plates 138, 140 are removably attached to brace 100. For example, the lateral and/or medial support plates 138, 140 can be insertable into a pockets in lateral and medial sides the body 102 or attached to the inner or outer surfaces of the body 102 by fasteners (such as hook and loop fasteners).

The lateral and/or medial support plates 138, 140 can be made from a heat formable material. The heat formable material can be substantially stiff or rigid at temperatures below a certain temperature and pliable or moldable at temperatures above the certain temperature. The lateral and/or medial support plates 138, 140 can thus be molded to conform to a particular wearer's anatomy by heating the lateral and/or medial support plates 138, 140 above the certain temperature such that they become pliable and moldable, fitting the brace 100 to the wearer such that the lateral and/or medial support plates 138, 140 conform to the patient's anatomy, and allow the lateral and/or medial support plates 138, 140 to cool below the certain temperature such that the lateral and/or medial support plates 138, 140 become substantially stiff or rigid. In some examples, the certain temperature is about 120, 130, 140, 150, 160, 170, 180, 190, or 200° F. Thus, in certain examples, the lateral and/or medial support plates 138, 140 are substantially stiff or rigid below 120, 130, 140, 150, 160, 170, 180, 190, or 200° F. and moldable or pliable above 120, 130, 140, 150, 160, 170, 180, 190, or 200° F.

The heat formable material can have a medium to high flexural modulus and/or a medium to high elongation or tensile strength. Suitable heat formable materials include polyester, polyethylene, polyvinyl chloride, polyethylene tetraphthalate, polyamide, or PVC foam such as Sintra™ or Komatex™, or combinations thereof. An example of a suitable heat-moldable material includes the material provided by DJO Global under the trademark Exos 40BX.

In an alternative example, the lateral and/or medial support plates 138, 140 are not heat moldable.

The lateral and/or medial support plates 138, 140 can provide rigidity or stiffness to the brace 100. The rigidity or stiffness can, for example, reduce or limit various motions of the foot 10 or ankle, such as eversion, inversion, internal rotation, external rotation, dorsiflexion, and/or plantarflexion.

The brace 100 can include a lateral buttress 142 (see FIG. 2A) and/or a medial buttress 144 (see FIG. 2B). The lateral buttress 142 and/or the medial buttress 144 can each be a small pad positioned above the lateral and/or medial malleolus 32, 34, respectively. In some examples, the lateral buttress 142 and/or the medial buttress 144 comprise foam, gel, or another cushioning material. In some examples, the lateral buttress 142 and/or the medial buttress 144 can comprise a heat moldable material as described above, such that the lateral buttress 142 and/or the medial buttress 144 can be molded to conform to the wearer's anatomy.

As illustrated in FIGS. 2A and 2B, the lateral buttress 142 and/or the medial buttress 144 can comprise an arcuate shape, configured to partially surround the lateral and/or medial malleolus 32, 34, respectively. Other shapes for the lateral buttress 142 and the medial buttress 144 are also possible.

In some examples, the lateral buttress 142 and/or the medial buttress 144 can be positioned, either removably (for example, via hook and loop fasteners) or fixedly, on the inner surface of the body 102. Accordingly, in FIGS. 2A and 2B, the lateral buttress 142 and the medial buttress 144 are illustrated using dashed lines.

Figure 3A:
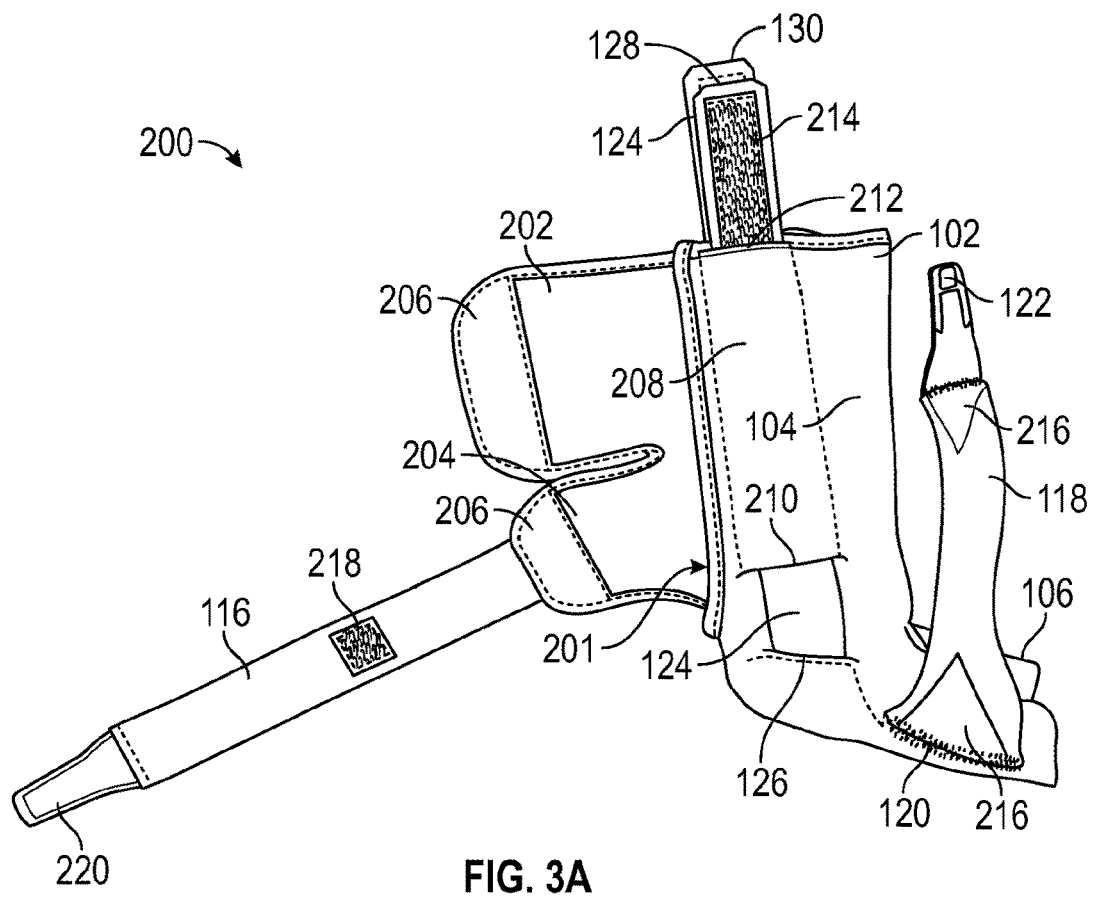
FIG. 3A is a lateral view of another embodiment of an ankle brace.

FIGS. 3A-4D illustrate another embodiment of a brace 200. FIGS. 3A and 3B are lateral and medial views of the brace 200 illustrated when not positioned on a wearer's ankle. FIGS. 4A-4D are lateral, medial, anterior, and posterior views of the brace 200 illustrated when positioned on the wearer's ankle. Similar to the brace 100, the brace 200 is configured for treatment and/or prevention of high ankle sprains. Again, although this disclosure primarily refers to high ankle sprains, the brace 200 may also be useful in treating and/or preventing other types of ankle sprains (such as inversion ankle sprains and/or eversion ankle sprains) and/or other types of ankle, foot, and/or lower leg injuries. FIGS. 3A-4D illustrate an example of the brace 200 configured to be worn on a right ankle. A mirror image of the illustrated brace 200 can be worn on a left ankle. The brace 200 is similar in many respects to the brace 100 previously described. Similar features of the brace 200 are referred to with the same reference numbers as used above with reference to the brace 100. These similar features will not be described again with reference to the brace 200 with the understanding that the description of these features given above is applicable to the similar features of the brace 200.

With reference to the lateral view of FIG. 3A, the brace 200 includes a posterior opening 201 formed on a posterior region of the leg portion 104 of the body 102. In some examples, the posterior opening 201 aids a wearer in donning the brace 200. For example, the wearer may insert the foot 10 and lower leg 11 through the posterior opening 201. As illustrated, the brace 200 also includes a first medial flap 202 and a second medial flap 204. The first and second medial flaps 202, 204 may include hook material 206 on the ends thereof. In some examples, the first and second medial flaps 202, 204 can be used to close the posterior opening 201 by wrapping the first and second medial flaps 202, 204 around the wearer's leg and attaching the hook material 206 to the lateral side of the brace 200.

The brace 200 can include a lateral pocket 208. The lateral pocket 208 can be formed on the lateral side of the brace. In certain embodiments, a lateral support plate 138 is positioned within the lateral pocket 208. As illustrated, the lateral pocket 208 can include a distal slit 210 and a proximal slit 212. The distal and proximal slits 210, 212 can allow access to the lateral pocket 208. In the illustrated embodiment, the lateral strap 124 extends through the lateral pocket 208. A distal end 128 of the lateral strap 124 extends from the distal slit 210 and includes a section of hook material 214. To tighten the lateral strap 124, the lateral strap can be pulled upwardly (proximally) and then folded back down (distally) and attached to the body 102 with the hook material 214.

As shown in FIG. 3A, the torsion strap 118 can include anchors 216 embedded therein. The anchors 216 can be fabric flags molded into the torsion strap 118. The anchors 216 can beneficially allow the torsion strap 118 to be sewn on its distal and proximal ends 120, 122, without tearing through the elastomeric material of the torsion strap 118.

The second tightening mechanism 116 can include regions of hook material 218, 220 on an inside surface thereof to facilitate attachment of the second tightening mechanism 116 to the body 102.

Figure 3B:
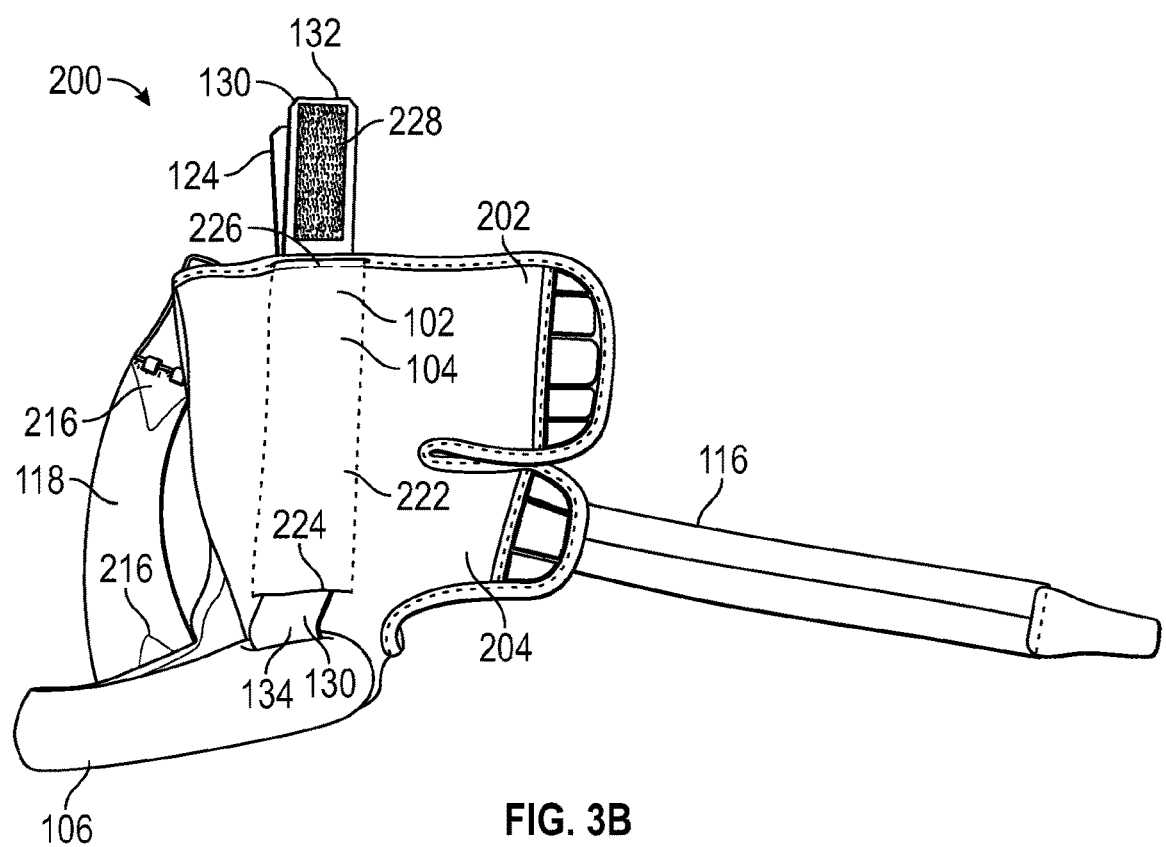
FIG. 3B is a medial view of the ankle brace of FIG. 3A.

With reference to the medial view of FIG. 3B, the brace 200 can include a medial pocket 222. The medial pocket 222 can be formed on the medial side of the brace 200. In certain embodiments, a medial support plate 104 is positioned within the medial pocket 222. As illustrated, the medial pocket 222 can include a distal slit 224 and a proximal slit 226. The distal and proximal slits 224, 226 can allow access to the medial pocket 222. In the illustrated embodiment, the medial strap 130 extends through the medial pocket 222. A distal end 132 of the medial strap 130 extends from the distal slit 226 and includes a section of hook material 228. To tighten the medial strap 130, the medial strap 130 can be pulled upwardly (proximally) and then folded back down (distally) and attached to the body 102 with the hook material 228.

FIGS. 4A-4D illustrate the brace 200 when worn. FIGS. 4A-4D are lateral, medial, anterior, and posterior views, respectively. With reference to FIGS. 4A-4D, when the brace 200 is worn, the first and second medial flaps 202, 204 are wrapped around the posterior of the lower leg 11 and attached to the lateral side of the brace. Lateral and medial straps 124, 130 extend from through lateral and medial pockets 208, 222 and are folded down and attached to brace 200. A first attachment mechanism 240 (shown in greater detail in FIG. 7) is attached to an anterior portion of the brace 200. the first attachment mechanism 240 includes a reel 110, a lace 112, and a lace guide 114 as described above.

The second attachment mechanism 116 extends from the second medial flap 204 and is wrapped around the lower leg 11. The torsion strap 118 connects the fifth metatarsal to the medial malleolus. Although not visible in FIGS. 4A-4D, the brace 200 can also include lateral and medial support plates 138, 140 and a footplate 136.

Figure 5:
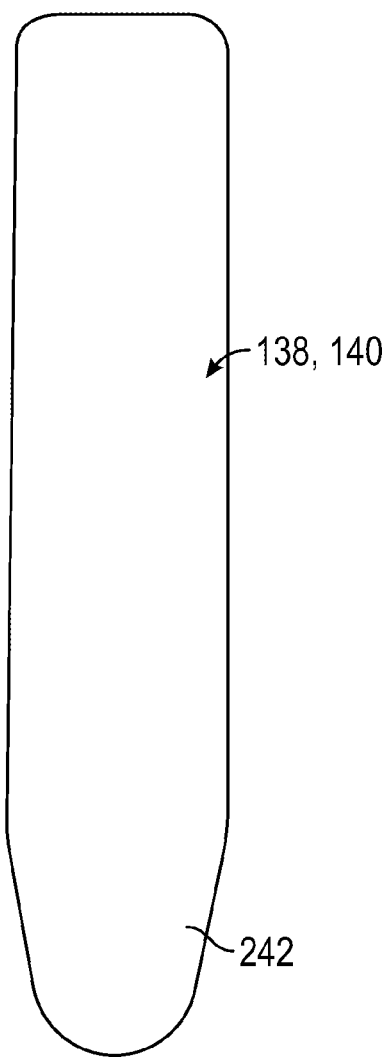
FIG. 5 is a view of an embodiment of a lateral or medial support plate.

FIG. 5 is a view of an embodiment of a lateral or medial support plate 138, 140. As shown, the lateral or medial support plate 138, 140 can include a tapered portion on an end thereof.

Figure 6A:
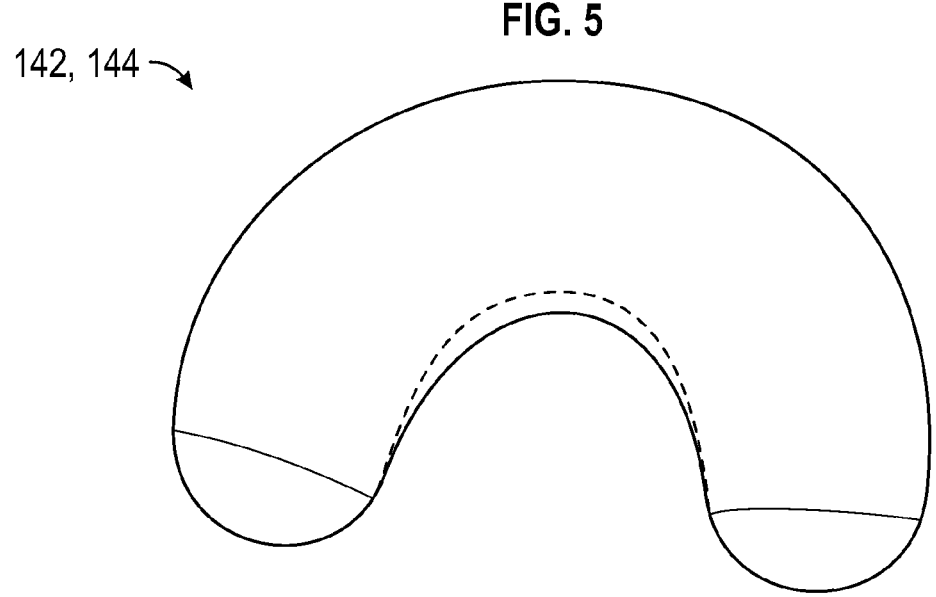
FIG. 6A is a view of an embodiment of a lateral or medial buttress.
Figure 6B:
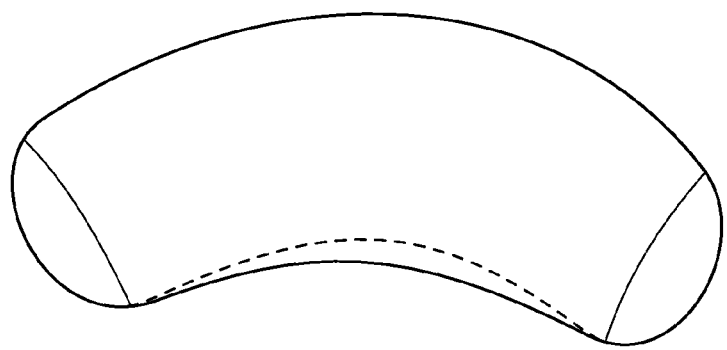
FIG. 6B is a view of another embodiment of a lateral or medial buttress.

FIGS. 6A and 6B are different embodiments of a lateral or medial buttress 142, 144. As shown, the lateral or medial buttress 142, 144 can comprise arcuate shapes. FIG. 6A illustrates an embodiment with a smaller radius of curvature. FIG. 6B illustrates an embodiment with a larger radius of curvature.

Figure 4A:
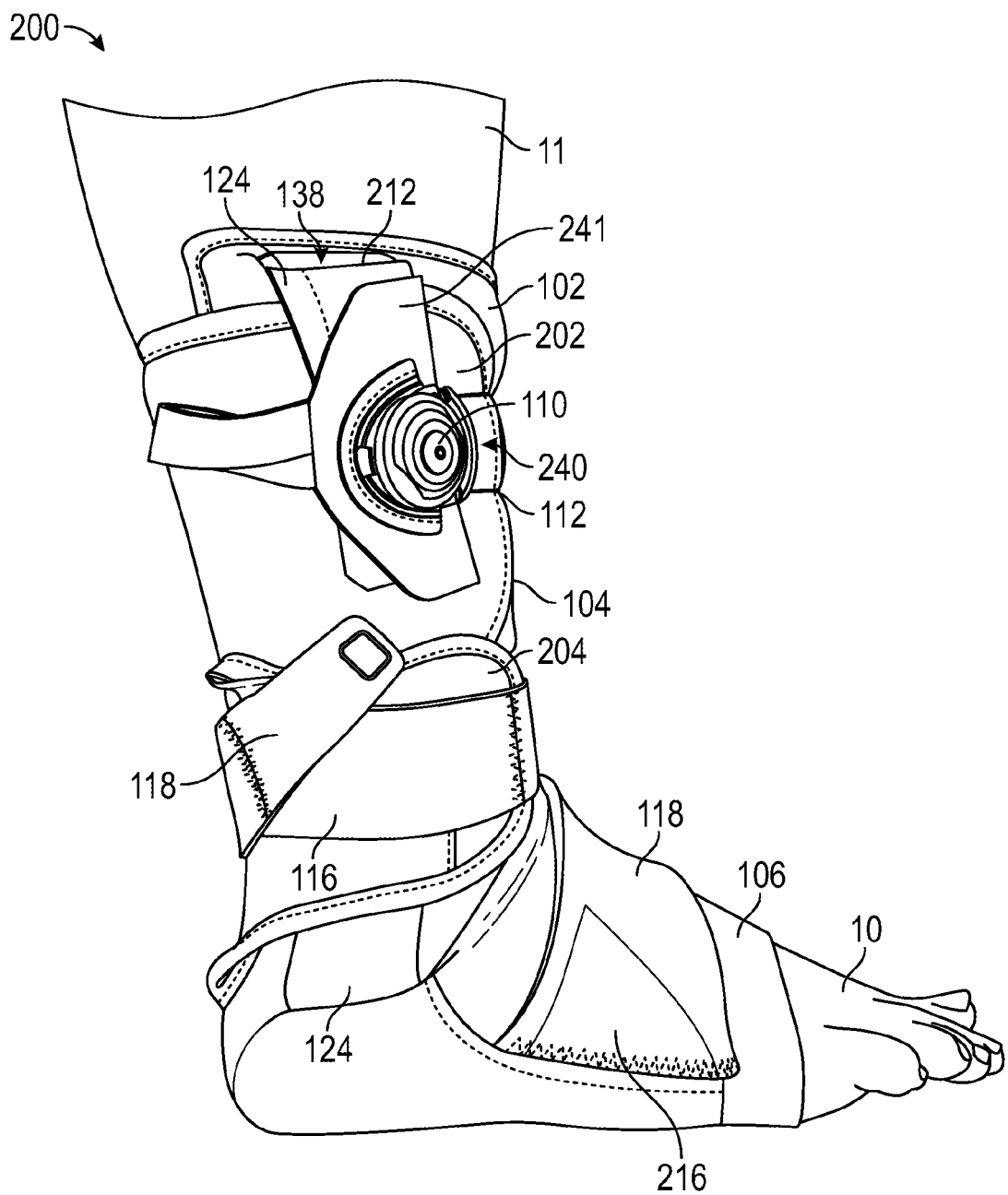
FIG. 4A is a lateral view of the ankle brace of FIGS. 3A and 3B, illustrated when worn on an ankle.
Figure 4B:
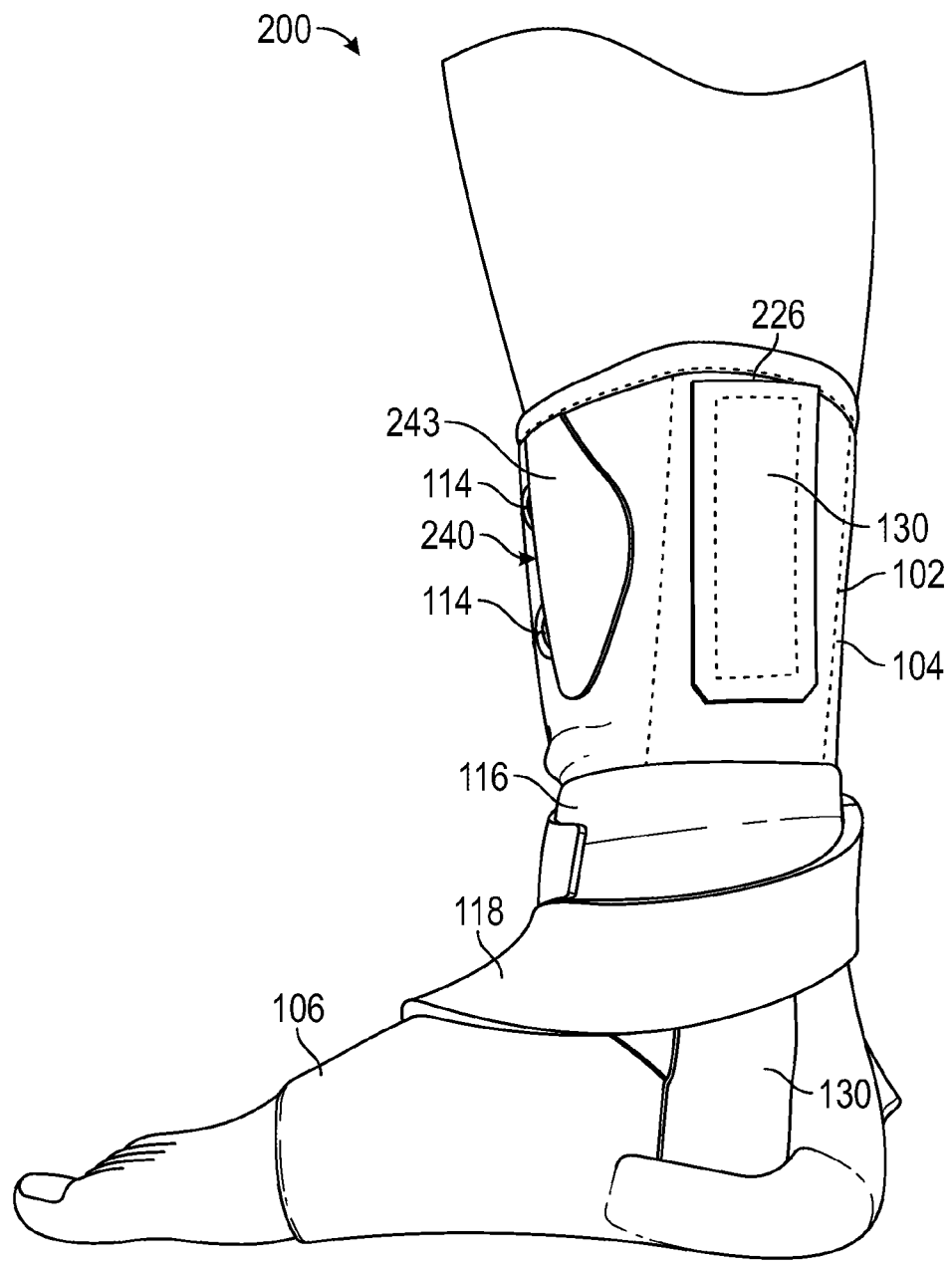
FIG. 4B is a medial view of the ankle brace of FIGS. 3A and 3B, illustrated when worn on an ankle.
Figure 4C:
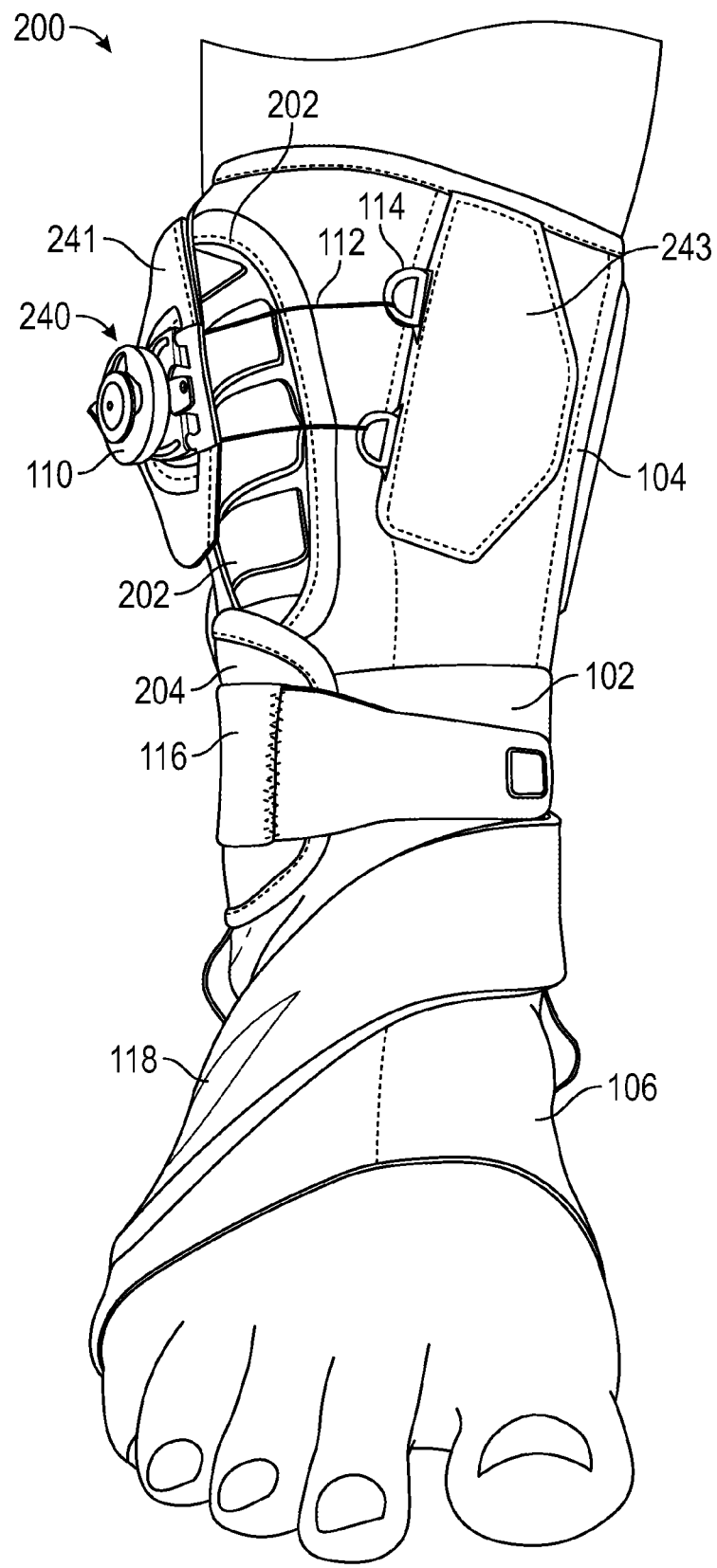
FIG. 4C is an anterior view of the ankle brace of FIGS. 3A and 3B, illustrated when worn on an ankle.
Figure 4D:
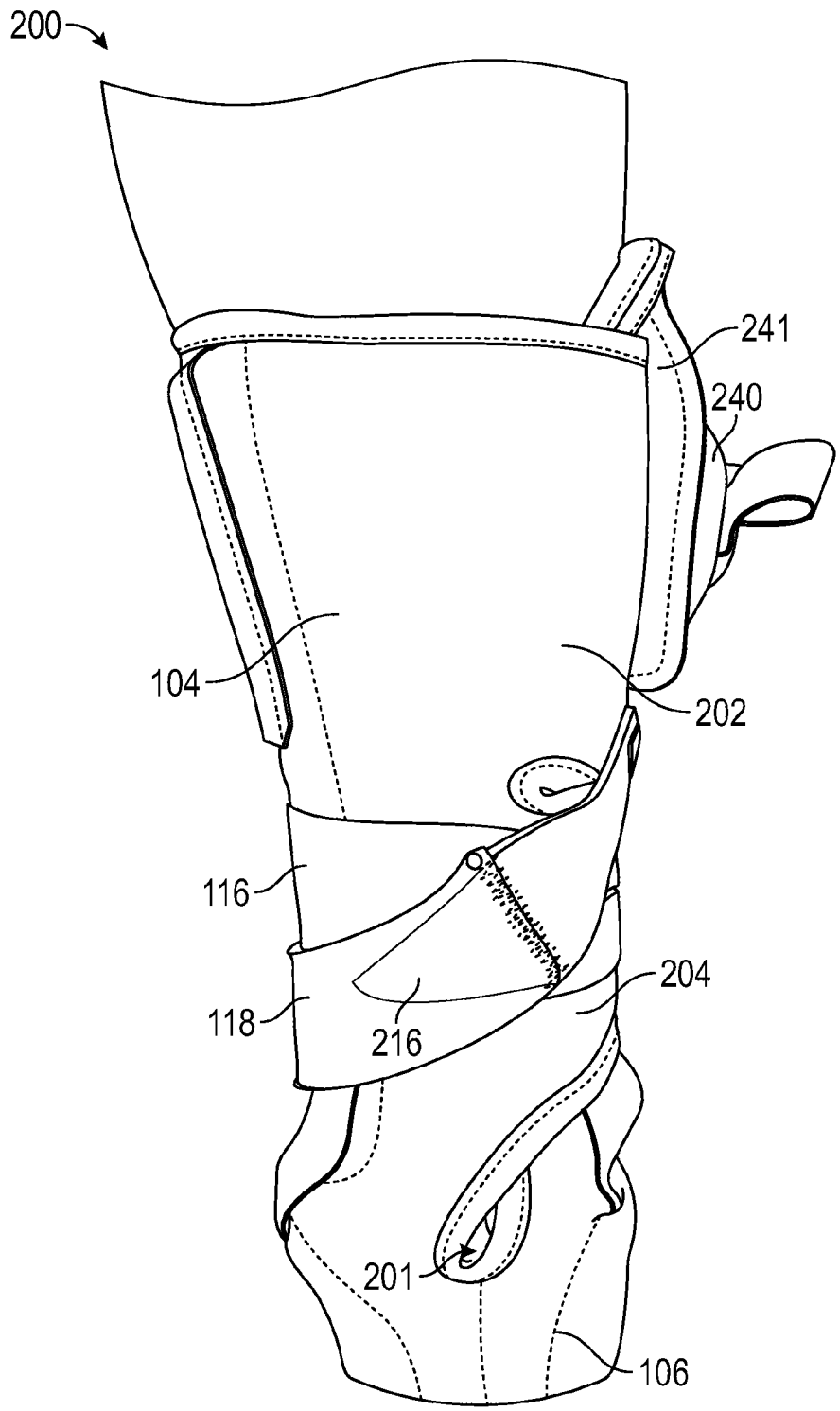
FIG. 4D is a posterior view of the ankle brace of FIGS. 3A and 3B, illustrated when worn on an ankle.
Figure 7:
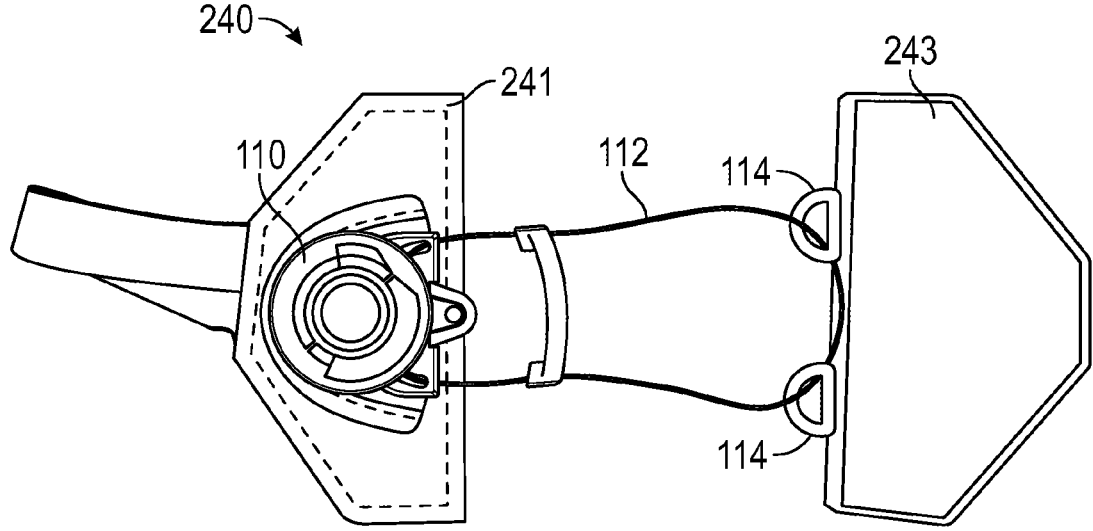
FIG. 7 is a view of an embodiment of a first tightening mechanism that can be used with various ankle braces described herein.

FIG. 7 is a view of an embodiment of a first tightening mechanism 240 that can be used with various ankle braces described herein, such as with the ankle brace 200 as shown in FIGS. 4A-4B. The first tightening mechanism 240 is configured to be removably attachable to the brace 200. The first tightening mechanism 240 includes a first tab 241 and a second tab 243. Each of the first and second tabs 241, 243 can include hook material on a rear surface thereof so as to be attachable to the body 102 of the brace 200. A reel 110 is positioned on the first tab 241. Lace guides 114 are positioned on the second tab 243. A lace 112 extends between the reel 110 and the lace guides 114. The reel 110 is actuable to tighten the brace to bring the first and second tabs 241, 243 together.

The foregoing description details certain embodiments of the systems, devices, and methods disclosed herein. It will be appreciated, however, that no matter how detailed the foregoing appears in text, the systems, devices, and methods can be practiced in many ways. As is also stated above, it should be noted that the use of particular terminology when describing certain features or aspects of the invention should not be taken to imply that the terminology is being re-defined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the embodiments. It will also be appreciated by those of skill in the art that parts included in one embodiment are interchangeable with other embodiments; one or more parts from a depicted embodiment can be included with other depicted embodiments in any combination. For example, any of the various components described herein and/or depicted in the figures may be combined, interchanged or excluded from other embodiments.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims. Applicant reserves the right to submit claims directed to combinations and sub-combinations of the disclosed inventions that are believed to be novel and non-obvious. Inventions embodied in other combinations and sub-combinations of features, functions, elements and/or properties may be claimed through amendment of those claims or presentation of new claims in the present application or in a related application. Such amended or new claims, whether they are directed to the same invention or a different invention and whether they are different, broader, narrower or equal in scope to the original claims, are to be considered within the subject matter of the inventions described herein.

What is claimed is:

1. An ankle brace comprising:
a body configured to be worn on an ankle and a foot of a wearer, the body including a foot portion and a leg portion, wherein the leg portion comprises
a lateral pocket configured to be positioned so as to extend over a lateral malleolus of the wearer, the lateral pocket accessible by a first lateral slit configured to be positioned below the lateral malleolus and a second lateral slit configured to be positioned above the lateral malleolus, and
a medial pocket configured to be positioned so as to extend over a medial malleolus of the wearer, the medial pocket accessible by a first medial slit configured to be positioned below the medial malleolus and a second medial slit configured to be positioned above the lateral malleolus;
a first tightening mechanism on the leg portion of the body, the first tightening mechanism actuable to tighten the leg portion of the body around a lower leg of the wearer;
a second tightening mechanism attached below the first tightening mechanism on the leg portion of the body, the second tightening mechanism actuable to tighten the leg portion of the body around the lower leg of the wearer;
a lateral strap comprising a distal end connected to a lateral side of the foot portion, the lateral strap configured to extend from the distal end through the first lateral slit, the lateral pocket, and the second lateral slit, and wherein a proximal end of the lateral strap is configured to be attached to the leg portion; and
a medial strap comprising a distal end connected to a medial side of the foot portion, the medial strap configured to extend from the distal end through the first medial slit, the medial pocket, and the medial lateral slit, and wherein a proximal end of the medial strap is configured to be attached to the leg portion.

2. The ankle brace of claim 1, further comprising a torsion strap configured to wrap around the body to limit external rotation of the foot of the wearer.

3. The ankle brace of claim 2, wherein the torsion strap is adjustable in tightness and positioning on the body.

4. The ankle brace of claim 1, further comprising a lateral buttress removably attachable to the foot portion of the body comprising a pad configured to partially surround the foot of the wearer.

5. The ankle brace of claim 1, further comprising a medial buttress removably attachable to the foot portion of the body comprising a pad configured to partially surround the foot of the wearer.

6. The ankle brace of claim 1, further comprising a removable footplate positioned on the body and configured to extend extending around a portion of the foot of the wearer.

7. The ankle brace of claim 6, wherein the footplate is comprised of a rigid material.

8. The ankle brace of claim 1, further comprising a lateral support plate extending along the lateral side of the ankle brace, wherein the lateral support plate is positioned inside the body.

9. The ankle brace of claim 8, wherein the lateral pocket is configured to hold the lateral support plate in the brace.

10. The ankle brace of claim 1, further comprising a medial support plate extending along the medial side of the ankle brace, wherein the medial support plate is positioned inside the body.

11. The ankle brace of claim 10, wherein the medial pocket configured to hold the medial support plate in the brace.

12. The ankle brace of claim 1, wherein the first tightening mechanism comprises:
   a reel attached to a first portion of the leg portion;
   a lace guide attached to a second portion of the leg portion; and
   a lace extending between the reel and the lace guide;
   wherein the reel is actuable to tighten the lace to bring the first portion toward the second portion.

13. The ankle brace of claim 1, wherein the second tightening mechanism comprises a detachable strap of elastomeric material.

14. The ankle brace of claim 1, wherein the body is comprised of an inside layer and an outside layer, and wherein the inside layer is in contact with the wearer.

15. The ankle brace of claim 14, wherein the outside surface is entirely comprised of a hookable material.

16. The ankle brace of claim 14, further comprising a space between the inside layer and the outside layer, the space configured to hold components of the ankle brace.

17. The ankle brace of claim 1, further comprising a posterior opening on a posterior region of the leg portion, the posterior opening configured to aid the wearer in putting on the ankle brace.

18. The ankle brace of claim 17, further comprising a set of medial flaps configured to hold the brace in a closed position once the wearer puts on the ankle brace.

19. The ankle brace of claim 1, wherein the lateral strap and the medial strap are comprised of an inelastic material.

20. The ankle brace of claim 1, wherein the first tightening mechanism is removably attachable to the body of the brace.

* * * * *

UNITED STATES PATENT AND TRADEMARK OFFICE
CERTIFICATE OF CORRECTION

| | |
|---|---|
| PATENT NO. | : 12,090,077 B2 |
| APPLICATION NO. | : 18/053918 |
| DATED | : September 17, 2024 |
| INVENTOR(S) | : Richard E. Gildersleeve |

It is certified that error appears in the above-identified patent and that said Letters Patent is hereby corrected as shown below:

In the Specification

Column 9, Line 4, delete "and or" and insert -- and/or --.

In the Claims

Column 14, Line 64, in Claim 6, after "extend" delete "extending".

Signed and Sealed this
Twenty-sixth Day of November, 2024

Katherine Kelly Vidal
*Director of the United States Patent and Trademark Office*